(12) United States Patent
Paroth et al.

(10) Patent No.: US 8,900,280 B2
(45) Date of Patent: Dec. 2, 2014

(54) SURGICAL INSTRUMENT

(76) Inventors: Christel Paroth, Tuttlingen (DE); Zbigniew Combrowski, Tuttlingen (DE); Alexander Henninger, Muhlheim (DE)

(\*) Notice: Subject to any disclaimer, the term of this patent is extended or adjusted under 35 U.S.C. 154(b) by 283 days.

(21) Appl. No.: 13/489,880

(22) Filed: Jun. 6, 2012

(65) Prior Publication Data
US 2013/0012954 A1  Jan. 10, 2013

(30) Foreign Application Priority Data
Jun. 9, 2011 (DE) .............................. 102011050996

(51) Int. Cl.
| | |
|---|---|
| *A61B 17/04* | (2006.01) |
| *A61B 17/86* | (2006.01) |
| *A61F 2/08* | (2006.01) |
| *A61B 17/70* | (2006.01) |
| *A61B 19/00* | (2006.01) |

(52) U.S. Cl.
CPC ......... *A61B 17/7037* (2013.01); *A61B 17/7085* (2013.01); *A61B 17/7091* (2013.01); *A61B 17/708* (2013.01); *A61B 17/8635* (2013.01); *A61B 2019/307* (2013.01); *A61B 17/7038* (2013.01)

USPC ............................................ 606/308; 606/319

(58) Field of Classification Search
USPC ................................................. 606/308, 319
See application file for complete search history.

(56) References Cited

U.S. PATENT DOCUMENTS

| | | | |
|---|---|---|---|
| 2008/0045953 A1* | 2/2008 | Garamszegi | 606/61 |
| 2012/0109224 A1* | 5/2012 | Biedermann et al. | 606/328 |

\* cited by examiner

*Primary Examiner* — Sameh Boles
(74) *Attorney, Agent, or Firm* — Dykema Gossett PLLC (57) ABSTRACT

A surgical instrument for seating a pedicle screw may comprise a driver head, a pressure ring, or at least one guide element. The driver head may be configured for removably connecting to the pressure ring or the at least one guide element, or a pressure ring and at least one guide element. The removable connection of the pressure ring or the at least one guide element from the driver head may be twistable or slidable for purposes of exchanging the pressure ring or the at least one guide element from the driver head. The pressure ring or at least one guide element is configured to operatively engage the pedicle screw and transfer motion of the surgical instrument to the pedicle screw.

17 Claims, 5 Drawing Sheets

SURGICAL INSTRUMENT

CROSS-REFERENCE TO RELATED APPLICATIONS

This application claims the benefit of priority to German Application No. 102011050996.8, filed Jun. 9, 2011, which is fully incorporated herein by reference as though fully set forth herein.

TECHNICAL FIELD

The invention generally relates to a surgical instrument.

BACKGROUND

The indications for a spondylodesis (stiffening) of the entire spinal column or adjacent vertebrae are very complex. Stabilizations, for example, are performed in case of degenerative change in the spinal column, after tumor removal, infections, or trauma.

In many cases, combinations of dorsal systems (e.g. rod-pedicle-screw systems) combined with multiple cages for ventral bracing are used for stabilizing the spinal column.

We know from biomechanics that the statics of the spinal column, as weight-bearing unit, can be compared with those of a crane. The anterior column, which consists of vertebrae and intervertebral discs, bears about 80% of the weight, the dorsal structures bear approx. 20%. From this we can deduct that the anterior portion of the lumbar spine is primarily subject to compressive forces, while the dorsal portion is primarily subject to tractive forces. In addition, shearing, torsional, and bending forces act on both columns.

While the above-mentioned screws/rod-systems are used in the dorsal area, a cage or implant is used for ventral bracing.

The goal of the stabilization of the vertebrae is a quick ossification of the intervertebral space, in order to achieve lasting freedom from pain for the patient.

Examples of the indication of a spondylodesis are: unstable vertebral fractures, degenerative instabilities, fractures with sufficient anterior bracing, dislocations, spinal tumors (without anterior defects), prior failed fusion (pseudoarthrosis).

The surgical techniques are carried out in open fashion or as minimally invasive procedures, depending on the indication. These procedures usually differ in size and type of access or accesses.

Accesses to the affected area can be gained through a combination of a ventral and dorsal access (in case of the cervical spine sometimes ventral only) or through a dorsal, dorsolateral, or lateral access.

An implant of the appropriate dimensions is chosen, depending on the structures and proportions found. Generally, the size is calculated in such a fashion that the screw reaches into the anterior third of the vertebral body.

Pedicle screws are screwed into the vertebral body through the pedicle. For safe navigation and guidance, some screws are cannulated and can be inserted through a guide wire. Some have additional cross-holes in the thread piece for subsequent cementing.

A rod, which connects two or more pedicle screw with each other, is inserted into the head of the screw, also called "tulip". The tulip can be rigid or movable in one or multiple directions, to facilitate the later insertion of the rod.

After the rod has been inserted on both sides, the vertebral bodies to be fixated are pressed apart with varying spreading systems, generally via the pedicle screws, to achieve the optimal distance between the vertebral bodies.

During this process, the mobility of the tulip can be obstructive if the objective is to raise vertebral bodies or reconstruct a physiological alignment (mainly in accident surgery).

Minimally invasive procedures require an extension of the tulip, to allow for the extracorporeal, percutaneous insertion of the rod.

Depending on the surgical technique, a variety of a manufacturer's screw forms and associated instrument sets are used.

It is disadvantageous that these consist of a variety of instruments because only experienced surgeons and surgical assistants can use this set of instruments without the manufacturing companies' product manager.

SUMMARY

The purpose of the invention is to provide an improved surgical instrument, which corrects the above-mentioned disadvantages.

The following features lead to the solution of the problem.

A surgical instrument includes a tulip, whereby the tulip features a pressure ring and/or guide element for receiving a pedicle screw. Preferably, the pressure ring is arranged on the tulip, in exchangeable fashion.

In typical design examples the guide element(s) is/are formed as single piece on the pressure ring.

In typical design examples the guide element(s) is/are a separate pieces. It is advantageous to use one or several pressure rings in combination with one or several guide elements, which is/are separate pieces.

Preferably, both the pressure ring and/or the guide element are formed as single pieces. This means that the pressure ring is formed as a component and/or the guide element is formed as a component, as well.

In alternative design examples the pressure ring and/or the guide element are formed as several pieces. This means that the pressure ring is composed of several individual pieces and/or the guide element is composed of several individual pieces, as well. This has the advantage that the guide elements or the pressure ring can be inserted into the tulip through recesses/holes. This is beneficial, as it allows for easy mounting and changing of the pressure ring and/or the guide element. For example, the pressure ring features an inner and/or outer ring.

In typical design examples the pressure ring and/or the guide element are twistable, and/or slidable. Preferably, the pressure ring is formed in such a way that the guide characteristics of the pressure ring are being changed by changing the position of the pressure ring. It is especially preferable that the pressure ring features one or several guide elements, which can mesh with a screw head, depending on the position of the pressure ring. This allows for different movements of the screw head or the screw, depending on the position of the pressure ring.

It is appropriate that the pressure ring and/or the guide element features a shaft. Preferably, the shaft is connected to the pressure ring and/or the guide element via a predetermined breaking point, making it possible to break off the shaft. This creates the advantage that the pressure ring and/or guide element can be easily twisted, slid, and/or exchanged.

It is appropriate that the pressure ring features a first guide element, with the guide element allowing a monoaxial motion of the pedicle screw, relative to the tulip.

Preferably, the pressure ring features a second guide element, which allows a polyaxial motion of the pedicle screw, relative to the tulip.

In typical design examples the pressure ring includes a third guide element, which rigidly fixates the tulip, relative to the pedicle screw.

In typical design examples the pressure ring and/or the guide element is connected to the tulip as individual piece. This is advantageous because no components have to be used.

Preferably, the guide elements are connected to the tulip and/or the pressure ring via a predetermined breaking point. This is advantageous because guide elements that are not required can be broken off. This is advantageous because it makes a pressure ring and/or a tulip suitable for rigid, monoaxial, and polyaxial bearing of the pedicle screw. For this, the guide elements that are not required can be broken off at the predetermined breaking points.

Preferably, the surgical instrument features a tulip extension, suitable for connecting with the extension shaft. It is particularly preferable that the design of the extension shaft, the tulip extension, and the tulip is always the same. This is advantageous because the pedicle screw and the tulip can be exchanged with its extension shaft in easy fashion. This is advantageous because the surgeon can always work with his or her familiar instrument, extension shaft, and/or handle.

It is appropriate that the tulip extension is connected to the tulip via a predetermined breaking point. This is advantageous because the tulip can be easily disconnected from the extension shaft via the tulip extension. It is also conceivable to shape the tulip with the tulip extension and the extension shaft from one piece.

It is an advantage if the extension shaft at least partially features an extension thread in its anterior area.

In typical design examples the tulip extension features a connection thread, at least in its posterior area. Preferably, the connection thread is suited to be in an operative connection with the extension thread. This is advantageous because the extension shaft and the tulip extension can be connected with each other in a simple fashion. It is appropriate that the connection thread or extension thread is preferably formed in the opposite rotational direction of the thread of the pedicle screw.

Preferably, the tulip extension and extension shaft are formed as individual pieces. It is especially preferable that the tulip extension is connected via a predetermined breaking point.

It is an advantage if the tulip, tulip extension, and extension shaft are formed as individual pieces. Preferably, the tulip, the tulip extension, and the extension shaft are connected via predetermined breaking points.

In alternative components, the tulip, tulip extension, and extension shaft are individual pieces, which are connected with each other via threads, sticks, notches, and/or glue.

In typical design examples the extension shaft is hollow. This is advantageous because this makes the extension shaft suitable for inserting the rod, a screwdriver, an Ini, a guide wire, and cement.

It is preferable that the screwdriver and/or the pedicle screw are cannulated. This is advantageous because this makes the components suitable for inserting the guide wire and/or cement. In addition, e.g. an internal thread or a coupling-like assembly, suitable for docking an instrument or cartridge for cementing, can be located in the cannulation of the pedicle screw.

The fastening of the pedicle screw can also happen via the extension shaft with e.g. the counterholder, in which case the screwdriver for the pedicle screw would not be needed. For this, the pedicle screw in e.g. the tulip must be clamped only, which can be achieved with a simpler, more affordable instrument, such as the cannulated screwdriver.

It is an advantage if the tulip extension has an internal thread. In the typical design examples the surgical instrument includes an Ini. Preferably, the Ini features a large adjustment track. This is advantageous because an adjustment is possible with as little as an Ini-drive and/or a t-handle, without additional instruments.

It is appropriate that the extension shaft and/or the tulip extension feature an exterior cone. Preferably, the breaking tool has an inner ring. It is particularly preferable that the inner ring is formed as a cone. This is advantageous because it makes the extension shaft also suitable for the procedural step of "breaking". If a breaking tool is positioned on the extension shaft and pressed downward via a lever that is not depicted, the extension shaft will break inwardly, at the tulip at the predetermined breaking point. The breaking can also occur laterally or outwardly.

Separately, protection is claimed for a pedicle screw for a surgical instrument, whereby the pedicle screw features a single screw head, which can be brought into operative connection with a first guide element and/or the second guide element and/or the third guide element of the pressure rings.

This is advantageous because, for choosing if no movement, a monoaxial movement, or polyaxial movement is to be allowed between tulip and pedicle screw, the same instrument set can be used and only the pressure ring has to be exchanged, accordingly, and that the pressure ring is attached to the tulip in exchangeable fashion.

Preferably, the pedicle screw is cannulated. It is particularly preferable that the pedicle screw includes a self-drilling tip, suitable for opening the pedicle. It is particularly preferable that the pedicle screw features a self-cutting thread. It is even more preferable that the pedicle screw features a partly cylindrical and or partly conical thread. This allows for several thread diameters, which are e.g. connected with each other via conical transitions.

The invention is especially advantageous when applied in a fashion where all pedicle screws feature a characteristic multi-functional extension shaft with identical design of the tulip, tulip extensions, and extension shafts.

Preferably, the pedicle screws are manufactured with different diameters of about 5 mm, 6 mm, 7 mm, with a length of 30 mm to 70 mm. The pedicle screws can be combined with tulips of polyaxial, monoaxial, or rigid design. Preferably, all pedicle screws are cannulated, self-cutting, and/or with diameters of 6 mm and 7 mm and cementable.

Preferably, the extension shaft serves as guide for the rod and rod insertion and, at the same time, provides the seal (Ini) for the rod, in pre-assembled fashion.

All steps of the procedure, such as screwing the pedicle screws, measuring the length of the rod, cementing if necessary, insertions of the rod, distraction and compression, raising the vertebrae for reconstructing physiological alignment, and rod fixation with the Ini are carried out via the extension shaft.

When all rods are fixated in the tulip, the rod inserter is decoupled from the rod. Now, the extension shaft can be detached via the SnapOff technique, i.e. the tulip extension from the tulip with the help of an instrument, without burr, extracorporeally.

All pedicle screws can be offered preferably with integrated Ini and drill wire, especially preferred in individual and sterile packaging.

Preferably, a small, clearly arranged, inventive instrument set that is the same for all surgical techniques features a drill wire, measuring instruments for the screw length via the drill wire, an instrument combining thread drill/pedicle opener, a screw driver/a drive for the Ini, a screwdriver/drives for the pedicle screw, a T-handle with ratchet with integrated torque limiter, an instrument for breaking off the tulip/extension shaft, a counterholder and/or an instrument for distraction and compression with rod length measurement.

In typical design examples the predetermined breaking point is formed as a ring, in one or more pieces. Typically the predetermined breaking point formed as several pieces is created because it is interrupted by e.g. openings intended for rod insertion and extraction. A predetermined breaking point formed in several pieces can also make it easier to separate the predetermined breaking point.

The preferred material for the pedicle screw, pressure ring, tulip, tulip extension, and the Ini is Titanium Grade 5.

Preferred manufacturing material for the extension shaft is stainless steel tubing. It is preferable that the extension shaft can be screw-fastened by positive connection with the tulip extension via a left-hand thread. Additional types of connecting are soldering, gluing, welding, and plugging.

Using the surgical instrument, which is designed according to the invention, results in important advantages for the surgeon. Pre-assembled implants can be used with Ini, the extension shaft can be used in multifunctional fashion, since it is the basis for all procedural steps, the system is cementable for open and minimally invasive surgical techniques. A slim, uniform instrument is provided for all surgical methods. All products look the same and are operated in the same manner for monoaxial, polyaxial, and rigid pedicle screws. This means there are few error sources and even untrained surgeons achieve a steep learning curve with this surgical instrument.

Preferably, the surgical instrument is offered in sterile individual packaging. Particularly preferable is the pedicle screw thread, which is formed in a manner that leads to maximal compression.

In typical design examples, which are not represented in more detail, the tulip or screw head includes formed pockets, which makes the pressure rings externally and internally switchable or twistable, slidable and pluggable, so that prior to sterile packaging, before or during the operation, the desired relative movement between tulip and screw head can be set, with the help of a pressure ring.

All possible elements between pressure ring and screw head, which provide degrees of freedom for rigid, monoaxial, or polyaxial movement, are permissible as guide elements.

A pressure ring can consist of a combination of two pressure rings, for example, or of a pressure ring or pressure rings with another part, whereby the inner or outer pressure ring can be, if necessary, prior to sterile packaging, before or during the operation, exchanged or selected, to achieve a different screw alignment.

The guide elements and the pressure rings can also be equipped with a breakable shaft with a SnapOff breaking point like the tulip, for the purpose of easy exchanging, twisting, sliding, etc.

BRIEF DESCRIPTION OF THE DRAWINGS

The following briefly describes the invention with help of the enclosed figures. The figures show.

DETAILED DESCRIPTION

Figure 1:
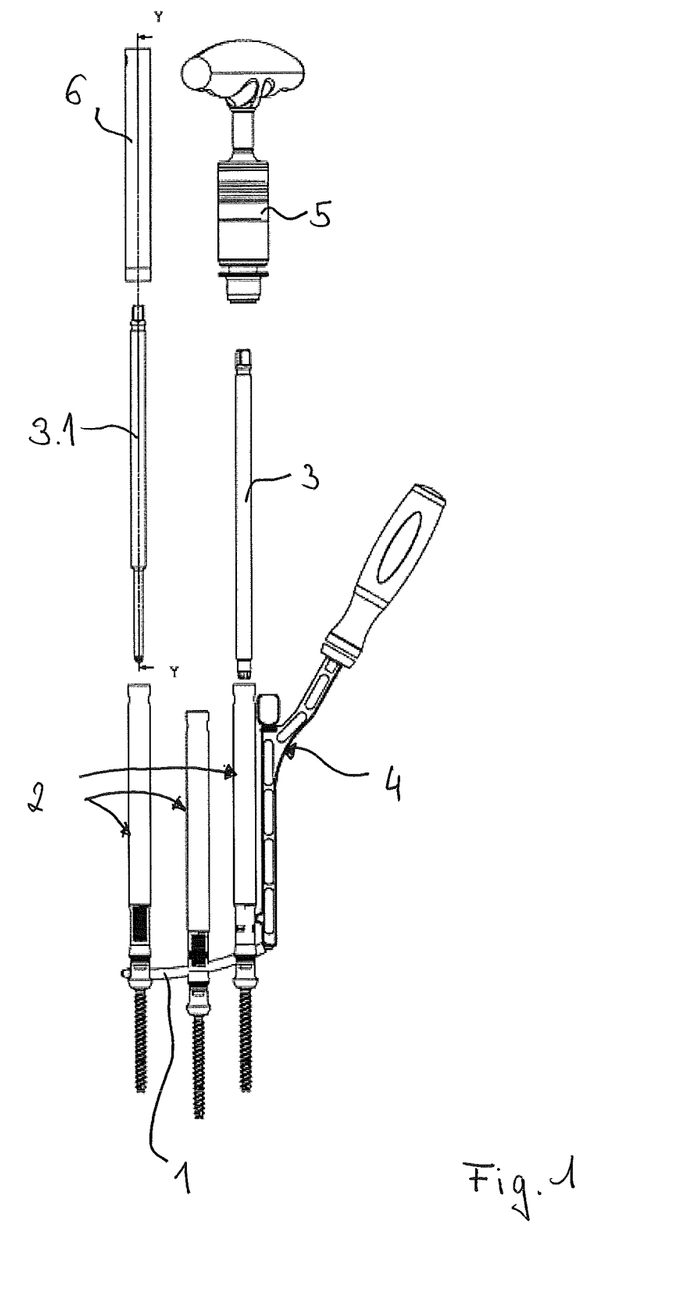
FIG. 1 shows a schematic representation of a set with an inventive surgical instrument, in an implant situation.

FIG. 1 shows a rod-pedicle screw system for stabilizing the spinal column. This system includes a rod 1, three screw units 2 as inventive surgical instrument, one screwdriver 3 for the Ini, one collet 4, one T-handle 5 with torque limiter, and an only partially represented breaking sleeve 6.

In FIG. 1 a screwdriver 3.1 for a pedicle screw is also represented.

Figure 2:
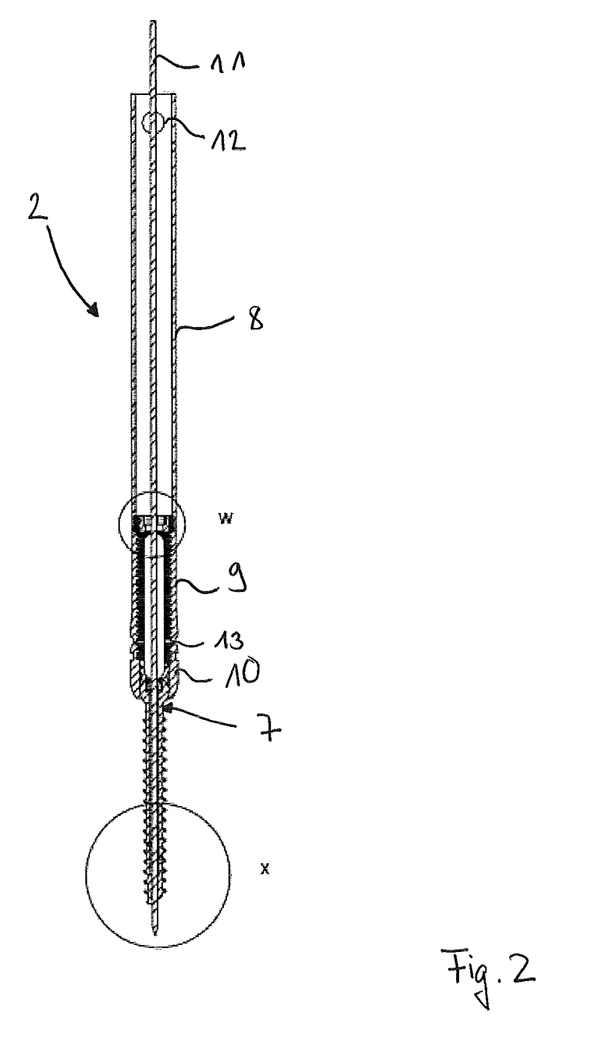
FIG. 2 shows a sectional representation of an inventive surgical instrument.

FIG. 2 shows an enlarged sectional representation of the screw unit 2. The screw unit 2 includes a pedicle screw 7 and an extension shaft 8, a tulip extension 9, and a tulip 10.

The extension shaft 8, the tulip extension 9, the tulip 10, and the pedicle screw 7 are cannulated. A guide wire 11 is inserted into the components. The extension shaft 8 has an opening 12 in an upper area, especially suited for counter-holding.

Figure 3:
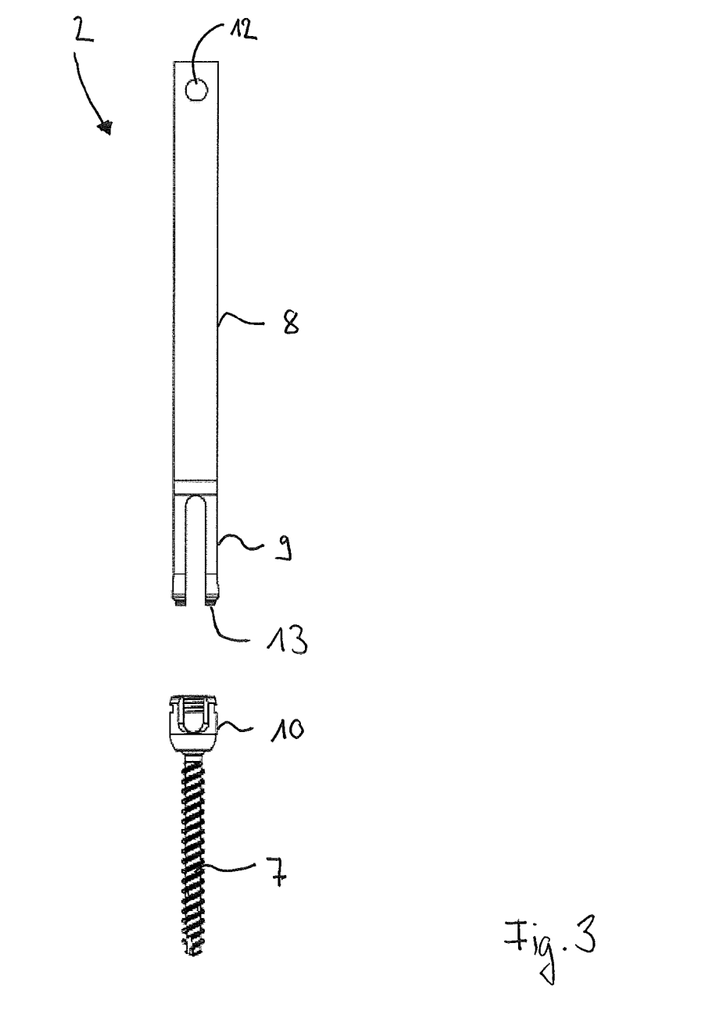
FIG. 3 shows a lateral view of the inventive surgical instrument, in which the instrument is separated at the predetermined breaking point.

The tulip extension 9 and the tulip 10 are connected via a predetermined breaking point 13. FIG. 3 shows the screw unit 2, in which the tulip extension 9 and the tulip 10 are separated at the predetermined breaking point 13.

Figure 4:
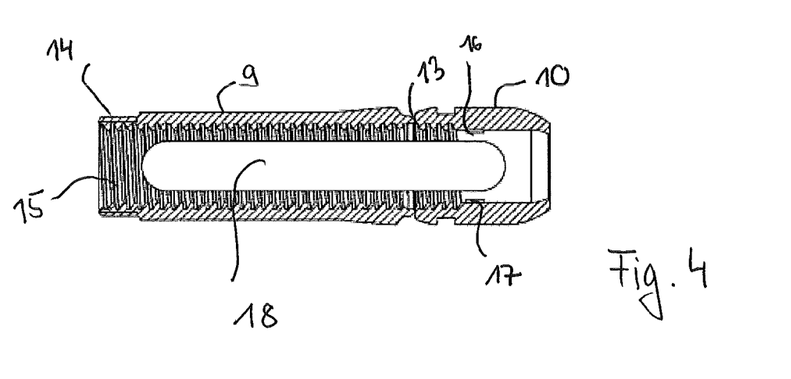
FIG. 4 shows a schematic representation of an enlarged, cut section of the inventive instrument.

FIG. 4 shows an enlarged sectional representation of the tulip extension 9 with the tulip 10, which are connected at the predetermined breaking point 13. The tulip extension 9 features a connection thread 14 at an exterior surface of a posterior area. Furthermore, the tulip extension 9 features an inner thread 15 on its interior surface. The connection thread 14 is a left-hand thread. The inner thread 15 is preferably a right-hand thread. The inner thread 15 reaches into an upper area of the interior surface of the tulip 10.

The tulip 10 features two retaining collars 16 and 17 on each interior surface, approximately at medium height. An oblong hole 18 is drilled into the tulip extension 9 and the tulip 10, suitable for receiving the rod 1.

Figures 5, 6, 7, 8, 9:
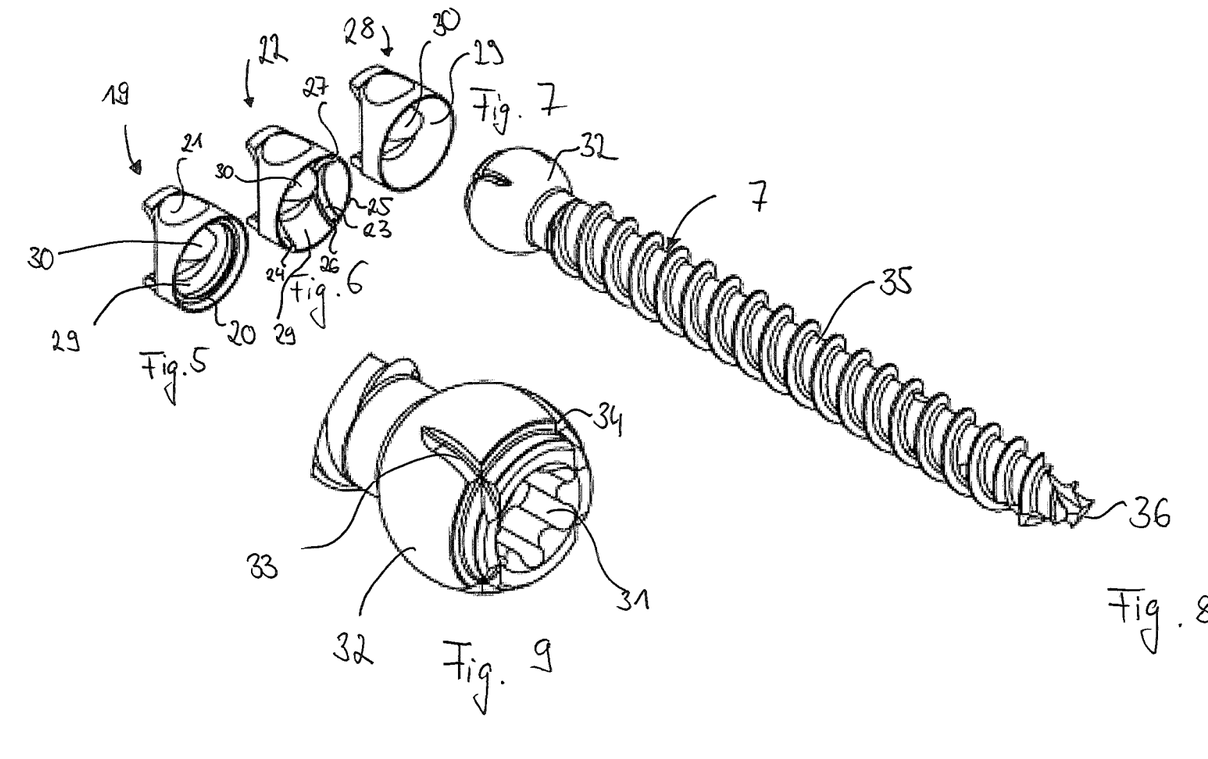
FIGS. 5 to 7 show different inventive design examples of a pressure ring for an inventive surgical instrument.
FIG. 8 shows a schematic representation of a pedicle screw for an inventive surgical instrument, in perspective view.
FIG. 9 shows the enlarged representation of a pedicles screw head, in perspective view.

FIG. 5 shows a first design example of a pressure ring 18. The pressure ring 19 shows a half-shell-formed interior surface with an opening 20. The pressure ring 18 is suitable for rigidly holding a pedicle screw 7. For this purpose, the pressure ring 18 features a circumferential notch 20 on its interior surface, as guide element. For the purpose of fixating the pressure ring 19 in the tulip 10, the pressure ring 18 features a recess 21, which the retaining collar 16 of the tulip 10 can grip, as represented in FIG. 4. Opposite to the recess 21, the pressure ring 19 features another recess that is not represented, which can be operatively connected with the retaining collar 17.

FIG. 6 shows another design example of a pressure ring 22, suitable for monoaxial holding of the pedicle screw 7. The pressure ring 22 is essentially formed analogous to the pressure ring 19. The pressure ring 19 has a half-shell-formed interior surface with an opening 20. The pressure ring 22 and the pressure ring 22 differ in the shape of the guide element. As guide element, the pressure ring 22 features a first bridge 23 and a second bridge 24. The bridges 23 and 24 are essentially arranged in symmetrical fashion. The bridge 23 has a semicircular arch-shaped form. The bridge 23 is fastened to an interior surface of the pressure ring, in such a fashion that the ends of the semicircular arch 26 and 27 end at one edge 25 of the pressure ring. The edge 25 is the edge, which faces the pedicle screw 7 at mounted screw unit 2.

FIG. 7 shows another design example of a pressure ring 28. The pressure ring 28 is essentially formed analogue to the pressure rings of the previous design examples and differs in its guide element. The pressure ring 28 allows for a polyaxial relative motion of the pedicle screw 7 relative to the tulip 10. For this, an interior surface 29 of the pressure ring 28 is formed as half-shell. The half-shell 29 features a hole 30 that is directed upwards.

The hole 30 in the half-shell 29 serves for using a polygon socket 31 in a screw head 32 of the pedicle screw 7, as represented in FIG. 9.

As recognizable in the enlarged representation of the screw head 32 in FIG. 9, the screw head 32 features guide elements, as well, which interact with the pressure rings 19, 22, and 28.

For all pressure rings 19, 22, and 28 the pedicle screw 7 can be used with a screw head 32 with the same form. The screw head 32 has a ball-shaped form, which allows it to interact with the half-shell-formed interior surface 29 of the pressure rings 19, 22, or 28 like a ball joint.

Furthermore, the screw head 32 features two grooves 33 and 34. The grooves 33 and 34 are formed as recesses on the screw head 32. The grooves 33 and 34 are essentially formed symmetrically. The grooves 33 and 34 run as half-circular arc on the lateral areas of the ball-shaped screw head 32. Hereby, the grooves 33 and 34 are positioned in such a way that they run onto the bridges 23 and 24 of the pressure ring 22. This allows for a monoaxial motion.

The pedicle screw 7 features a thread at its pedicle screw shaft 35. The thread is preferably double-threaded, self-drilling and/or self-cutting.

Especially a tip 36 of the pedicle screw shaft 35 is self-cutting and self-drilling. Furthermore, the pedicle screw shaft 35 is preferably cone-formed, so that the pedicle screw shaft 35 has a smaller diameter at an anterior area of the tip 36 than in a posterior area, close to the screw 32 head.

Preferably, the pedicle screw 7 is cannulated, as can be recognized in FIG. 2, for example. This has the advantage that e.g. a guide wire 11 can be inserted through the pedicle screw 7 and the pedicle screw 7 is also suitable for introducing cement. Preferably the pedicle screw 7 features continuous holes in its pedicle screw shaft 35, through which the cement, which is introduced through the cannula of the pedicle screw 7, flows outwardly into the vertebral body and is able to join with it.

Figure 10:
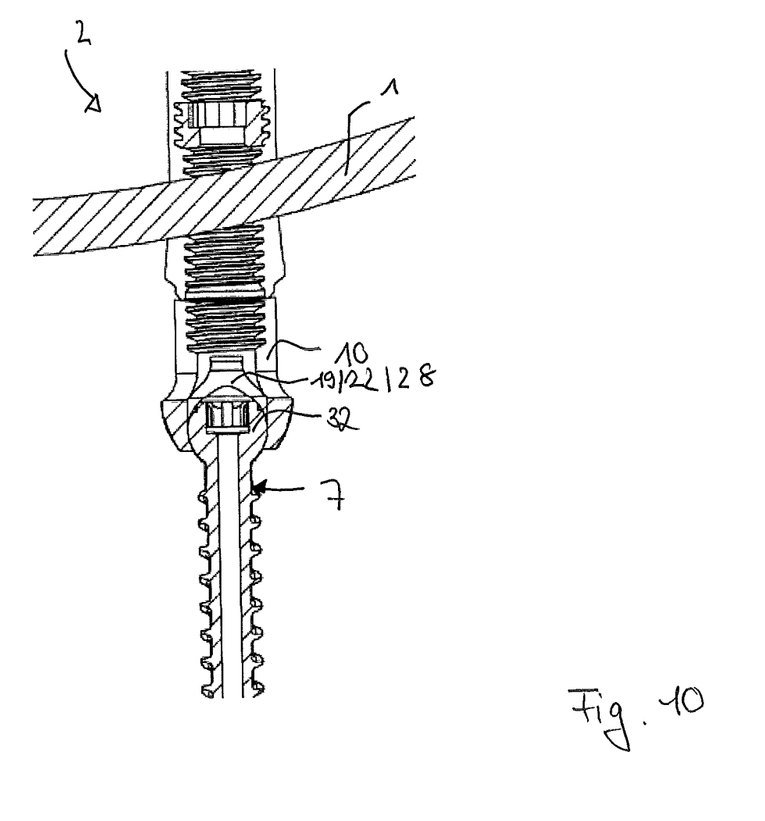
FIG. 10 shows an enlarged, cut section of an inventive surgical instrument according to FIG. 1.

The FIG. 10 shows a cut and enlarged section of the screw unit 2 with part of the rod 1 according to FIG. 1. It is recognizable that the pedicle screw 7 with the pedicle screw head 32 is inside the tulip 10. One of the pressure rings 19, 22, or 28 is inserted into the tulip 10 and allows for the desired movement of the pedicle screw 7.

The invention at hand has the following functionality:

The screw elements 2 can be used in open or minimally invasive fashion, depending on indication. After determining the implant dimensions, the correct position for the pedicle screw 7 is identified, preferably in x-ray mode with a Jamshidi-needle or the guide wire 11.

Subsequently, the guide wire 11 and/or a portal are used. For controlling the pedicle screw length, additional non-represented measuring instruments can be used via the drill wire 11 to determine or compare the screw length.

The opening of the pedicle and the cutting of the thread preferably happen directly with the self-cutting thread of the pedicle screw 7 at the pedicle screw shaft 35. The cannulated pedicle screw 7 contains the polygon socket 31 in the screw head 32, preferably torx-like, and is securely inserted and screwed into the vertebral body, through the pedicle via the guide wire 11.

In the case of brittle, hard bones or brittle bone disease the opening of a pedicle and the thread cutting should be done with a combination instrument. Preferably, different designs of a thread drill are used.

In case of a lack of compression or osteoporose vertebral bodies cement can be inserted through the cannulated pedicle screw 7, after screwing in.

During the percutaneous inserting of the rod 1, the rod 1 is inserted from above through the extension shaft 8 and once again extracted from one side through the oblong hole 18 in the tulip extension 9 or the tulip 10 and guided through the vertebral body. This makes it possible to connect two or more vertebral bodies with each other, with a rod 1 up to a length of approx. 120 mm.

Next follows the necessary distraction or compression via the extension shaft 8, in extracorporeal fashion, as well as the raising of the vertebral bodies, to reconstruct a physiological alignment.

The distraction or compression is achieved with the help of an instrument, which is adjustable alongside the extension shaft 8. This instrument also serves to determine the length of the rod 1.

A necessary raising of vertebral bodies preferably happens only via the pre-assembled Ini with large adjustment track and only with an Ini-drive 3 and the T-handle 5, without additional instruments.

When all rods are fixated in the tulips 10 of the screw units 2 and tightened to the specified torque, the extension shaft 8 can be broken off at the predetermined breaking point 13, the so-called SnapOff-connection, with a non-represented instrument, without burr. Alternatively, the breaking sleeve 6 is used for this.

In further design examples a tulip extension shaft breaking tool is used in extracorporeal fashion.

A non-represented counterholder can be put on the extension shaft 8, in extracorporeal fashion, for tightening the Ini to the specified torque. For this purpose, the extension shaft 8 features the opening 12.

The extension shaft 8 has an external cone, above the predetermined breaking point 13 on the tulip extension 9 and the breaking tool features an inner ring, which preferably is cone-formed. If the breaking tool is put on extension shaft 8 and e.g. pressed down via a non-represented lever, the extension shaft 8 breaks off inwardly at the tulip 10 at the predetermined breaking point 13. Breaking off the tulip 10 can also happen outwardly or laterally, however. For this purpose, an instrument can be used, which partially cuts or crops at the predetermined breaking point 13.

As soon as the rods 1 have been tightened to the specified torque, the rod inserter can be decoupled from the rod and removed from the body, as well.

The invention claimed is:

1. A surgical instrument for seating a pedicle screw, the surgical instrument comprising: a pressure ring or at least one guide element, or a pressure ring and at least one guide element, wherein the pressure ring or the at least one guide element, or a pressure ring and at least one guide element, is configured to operatively engage the pedicle screw and transfer motion of the surgical instrument to the pedicle screw; and a driver head configured for removably connecting to the pressure ring or the at least one guide element, or a pressure ring and at least one guide element, wherein the removable connection of the pressure ring or the at least one guide element, or a pressure ring and at least one guide element, from the driver head is twistable or slidable for purposes of exchanging the pressure ring or the at least one guide element, or a pressure ring and at least one guide element from the driver head, wherein a first guide element or a second guide element or a third guide element is integrally formed with the pressure ring, wherein the first guide element is configured to allow for a monoaxial motion of the pedicle screw relative to the driver head, the second guide element is configured to allow for a polyaxial motion of the pedicle screw relative to the driver head, and the third guide element is configured to rigidly fixate the driver head to the pedicle screw.

2. The surgical instrument of claim 1, wherein the pressure ring has a shaft breakable along a predetermined break point which is removable from the driver head after separation of the shaft from the pressure ring.

3. The surgical instrument of claim 1, wherein the at least one guide element is integrally formed with the pressure ring.

4. The surgical instrument of claim 3, wherein a first guide element is integrally formed with the pressure ring, and the first guide element is configured to allow for a monoaxial motion of the pedicle screw relative to the driver head.

5. The surgical instrument of claim 3, wherein a second guide element is integrally formed with the pressure ring, and the second guide element is configured to allow for a polyaxial motion of the pedicle screw relative to the driver head.

6. The surgical instrument of claim 3, wherein a third guide element is integrally formed with the pressure ring, and the third guide element is configured to rigidly fixate the driver head to the pedicle screw.

7. The surgical instrument of claim 1, wherein a portion of the driver head comprises a driver head extension, wherein the driver head extension is configured to connect to an extension shaft.

8. The surgical instrument of claim 7, wherein the driver head extension has an internal thread.

9. The surgical instrument of claim 7, wherein the driver head extension is separately connectable from the other portion of the driver head via a predetermined breaking point.

10. The surgical instrument of claim 9, wherein a portion of the driver head has a cone shape proximate the predetermined breaking point and the cone shape portion is configured to engage a breaking tool having an inner ring corresponding to the cone shape.

11. The surgical instrument of claim 9, wherein a portion of the extension shaft is cone shape proximate the predetermined breaking point and the cone shape portion is configured to engage a breaking tool having an inner ring corresponding to the cone shape.

12. The surgical instrument of claim 1, further comprising an extension shaft having a threaded anterior portion, wherein the threaded anterior portion of the extension shaft is configured to removably connect to the driver head.

13. The surgical instrument of claim 12, wherein the extension shaft is removable connectable to a driver head extension portion of the driver head via the threaded anterior portion of the extension shaft and a corresponding threaded posterior portion of the driver head extension portion of the driver head.

14. The surgical instrument of claim 12, wherein the extension shaft is hollow.

15. The surgical instrument of claim 12, wherein the driver head is hollow.

16. The surgical instrument of claim 1, further comprising a driver head extension separate from the driver head, wherein the driver head extension is configured to connect to an extension shaft and the driver head.

17. The surgical instrument of claim 1, wherein an Ini having a large adjustment track is pre-assembled.

* * * * *